United States Patent
Gobron et al.

(10) Patent No.: US 11,377,471 B2
(45) Date of Patent: Jul. 5, 2022

(54) PROCESS FOR THE PREPARATION OF A DODECAPEPTIDE

(71) Applicant: AXOLTIS PHARMA, Clermont-Ferrand (FR)

(72) Inventors: Stéphane Gobron, Dallet (FR); Dominique Bridon, San Francisco, CA (US); Frédéric Cabart, Lingoslheim (FR); Christian Fauster, Gerstheim (FR)

(73) Assignee: AXOLTIS PHARMA, Clermont-Ferrand (FR)

( * ) Notice: Subject to any disclaimer, the term of this patent is extended or adjusted under 35 U.S.C. 154(b) by 0 days.

(21) Appl. No.: 16/485,064

(22) PCT Filed: Feb. 9, 2018

(86) PCT No.: PCT/EP2018/053358
§ 371 (c)(1),
(2) Date: Aug. 9, 2019

(87) PCT Pub. No.: WO2018/146283
PCT Pub. Date: Aug. 16, 2018

(65) Prior Publication Data
US 2020/0002374 A1 Jan. 2, 2020

(30) Foreign Application Priority Data
Feb. 10, 2017 (EP) .................... 17305154

(51) Int. Cl.
*C07K 7/08* (2006.01)
*C07K 1/18* (2006.01)

(52) U.S. Cl.
CPC . *C07K 1/18* (2013.01); *C07K 7/08* (2013.01)

(58) Field of Classification Search
None
See application file for complete search history.

(56) References Cited

U.S. PATENT DOCUMENTS

| | | |
|---|---|---|
| 10,646,589 B2 | 5/2020 | Jansson et al. |
| 2008/0287650 A1 | 11/2008 | Tovi et al. |
| 2010/0280221 A1 | 11/2010 | Callens et al. |
| 2011/0178023 A1 | 7/2011 | Meiniel et al. |
| 2016/0175457 A1 | 6/2016 | Edens et al. |
| 2018/0264139 A1 | 9/2018 | Jansson et al. |
| 2018/0265549 A1 | 9/2018 | Bridon et al. |

FOREIGN PATENT DOCUMENTS

| | | |
|---|---|---|
| JP | A-2014-162722 | 9/2014 |
| WO | WO-1999/003890 | 7/1998 |
| WO | WO-2008/090285 | 12/2007 |
| WO | WO 2008/109079 | * 9/2008 |
| WO | WO-2015036576 | 3/2015 |

OTHER PUBLICATIONS

Andreu et al. ('Formation of disulfide bonds in synthetic peptides and proteins' from Methods in Molecular Biology v35 Peptide synthesis Protocols 1994 Chapter 7 pp. 91-169). (Year: 1994).*
Isidro-Llobet et al. ('Amino acid-protecting groups' Chem Rev v109 2009 pp. 2455-2504). (Year: 2009).*
International Search Report for International Application No. PCT/EP2018/053358, dated Apr. 18, 2018, European Patent Office, Rijswijk, NL.
European Search Report for European Application No. EP 17 30 5154, dated Jul. 24, 2017, European Patent Office, The Hague, NL.
Sakka L et al.: "SCO-spondin derived peptide NX210 induces neuroprotection in vitro and promotes fiber regrowth and functional recovery after spinal cord injury", PLOS One, Public Library of Science, vol. 9, No. 3, Mar. 25, 2014 (Mar. 25, 2014), pp. e93179-1, XP002734572, ISSN: 1932-6203, DOI: 10.1371/JOURNAL.PONE.0093179 [retrieved on Jan. 1, 2014], p. 2, col. 1, line 54-line 62.
Cebrian J et al.: "Synthesis and biological activity of thrombospondin related peptides", Current Topics in Peptide & Protein Rese., vol. 4, Jan. 1, 2001 (Jan. 1, 2001), pp. 81-88, XP009119150, ISSN: 0972-4524, p. 82, col. 1, line 43-col. 2, line 49.
Trivedi et al.: "The role of thiols and disulfides in protein chemical and physical stability", Dec. 2009, pp. 614-625, vol. 10(6), Curr Protein Pept Sci.
Meiniel, Annie: "SCO-Spondin, a Glycoprotein of the Subcommissural Organ/Reissner's Fiber Complex: Evidence of a Potent Activity on Neuronal Development in Primary Cell Cultures", 2001, pp. 484-495, vol. 52, Microscopy Research and Technique.
Gobron et al.: "Subcommissural Organ/Reissner's Fiber Complex: Characterization of SCO-Spondin, a Glycoprotein With Potent Activity on Neurite Outgrowth", 2000, pp. 177-191, vol. 32, GLIA.
Bitar et al.: "Effects of SCO-spondin thrombospondin type 1 repeats (TSR) in comparison to Reissner's fiber material on the differentiation of the B104 neuroblastoma cell line", 2001, pp. 361-369, vol. 304, Cell Tissue Res.
Isidro-Llobet, et al, "Amino Acid-Protecting Groups", 2009, pp. 2455-2504, vol. 109, Chem. Rev.

* cited by examiner

*Primary Examiner* — Ronald T Niebauer
(74) *Attorney, Agent, or Firm* — B. Aaron Schulman, Esq.; Stites & Harbison, PLLC (57) ABSTRACT

The invention concerns an improved process for the preparation of the dodecapeptide NX210 of SEQ ID NO: 1 in which the formation of side products is minimized.

8 Claims, 4 Drawing Sheets
Specification includes a Sequence Listing.

Minutes

PROCESS FOR THE PREPARATION OF A DODECAPEPTIDE

The present invention is directed to a process for preparing the peptide NX210.

NX210, a dodecapeptide of sequence Trp-Ser-Gly-Trp-Ser-Ser-Cys-Ser-Arg-Ser-Cys-Gly (W-S-G-W-S-S-C-S-R-S-C-G, SEQ ID NO: 1) derived from the most conserved sequence of the thrombospondine type 1 repeats (TSR) found in the SCO-spondin, is a candidate for the treatment of neurological disorders, due in particular to its capacity to induce cell differentiation and neural growth, along with its capacity to promote cell survival.

As number of oligopeptides and polypeptides containing several cysteines, NX210 is subject to oligomerization and more particularly to intramolecular cyclization. This latter reaction leads to the formation of a cyclized metabolite (NX218, containing a disulfide bridge between the two cysteines) possessing biological properties distinct from that of NX210.

Manufacturing process to obtain acceptable quality of product is of particular importance especially in case of injectable drugs as presence of the synthesis impurities might seriously affect the efficacy or the safety of the drug products. Thus, the medicinal products must have a very high purity and any secondary products must be precisely characterized. As a result, the rules imposed by the health authorities are extremely severe, for obvious reasons of patient safety.

NX210 consists of amino acids known to be problematic during peptide syntheses: cysteine residues can lead to the oligomerization and cyclization mentioned above once the thiol function has been liberated; cysteine and tryptophan are sensitive to acidic conditions such as the ones encountered during deprotection of the peptide with trifluoroacetic acid); conventional protective groups for the side chain of arginine residues (such as 2,2,5,7,8-pentamethyl-chroman-6-sulphonyl (pmc)) or 4-methoxy-2,3,6-trimethylbenzene-sulfonyl (Mtr) lead, during deprotection, to highly reactive intermediates capable of reacting with the side chain of other amino acids and require reaction times incompatible with the other amino acids.

The synthesis of oligopeptides containing such problematic amino acids therefore requires the use of more or less complex cleavage cocktails (i.e. containing more or fewer reagents) allowing deprotection of the side chains of all the amino acids, while avoiding the degradation of the peptide.

By way of example, mention of the following cocktails may be made:
 the mixture of trifluoroacetic acid (88% v/v), phenol (5% v/v), water (5% v/v) and triisopropylsilane (2% v/v) (Reagent B),
 the mixture of trifluoroacetic acid (81% w/w), phenol (5% w/w), thioanisole, (5% w/w), 1,2-ethanedithiol (2.5% w/w), water (3% w/w), dimethyl sulfide (2% w/w) and ammonium iodide (1.5% w/w) (Reagent H),
 the mixture of trifluoroacetic acid (82.5% v/v), phenol (5% v/v), water (5% v/v), thioanisole (5% v/v) and 1,2-ethanedithiol (2.5% v/v) (Reagent K),
 the (low odour) mixture of trifluoroacetic acid (88% v/v), triisopropylsilane (2% v/v), 1,4-dithiothreitol (5% w/v) and water (5% w/v) (Reagent L),
 the mixture of trifluoroacetic acid (90% v/v), thioanisole (5% v/v), 1,2-ethanedithiol (3% v/v) and anisole (2% v/v) (Reagent R).

Ideally the cocktail used should also be capable of leading to the cleavage of the peptide from the resin to which the peptide is attached at the end of the solid phase synthesis sequence.

In the case of a polypeptide such as NX210 containing multiple problematic amino acids, the choice of a deprotection cocktail is therefore far from trivial, in particular when the purity of the final product must be closely controlled.

In addition thereto, conditions liable to minimize the dimerization and/or oligomerization of the peptide during its preparation are highly desirable.

A first object of the present invention is a method for isolating NX210 making it possible to limit the formation of the cyclic form of NX210.

A second object of the present invention is a process characterized by the use of amino acids carrying protective groups on the side chain compatible with the final deprotection step, in particular protective groups making it possible to limit the formation of oligomers of NX210 or the cyclic form of NX210 (known as NX218).

A third object of the present invention is a method for isolating NX210 making it possible to limit the formation of the cyclic form of NX210.

As is well known to those skilled in the art, all the steps of the process are carried out under an inert atmosphere in order to avoid the oxidation of the sulfur atoms of the cysteines of NX210, (unless otherwise indicated).

In a first embodiment, the present invention concerns a process for preparing a peptide of SEQ ID NO: 1, characterised in that the peptide of SEQ ID NO: 1 is constantly maintained in an aqueous solution comprising an organic solvent throughout the steps of purification, optional concentration and drying, the latter step being advantageously performed by freeze-drying or spray-drying, of the peptide of SEQ ID NO: 1.

The present invention also concerns a process for preparing a peptide of SEQ ID NO: 1, characterised in that the purification and/or drying, advantageously by freeze-drying or spray-drying, of the peptide of SEQ ID NO: 1 are carried out in an aqueous solution comprising an organic solvent.

In a totally unexpected manner, the Inventors have evidenced that the presence of an organic solvent in the aqueous solutions containing the peptide of SEQ ID NO: 1 during the steps of purification and drying of the peptide of SEQ ID NO: 1 prevents the formation of side products, in particular of the cyclized form of the peptide of SEQ ID NO: 1.

In the sense of the present invention, what is meant by i) "the peptide of SEQ ID NO: 1 is constantly maintained in an aqueous solution comprising an organic solvent throughout the steps of purification, optional concentration and drying, the latter step being advantageously performed by freeze frying or spray-drying" and ii) "the steps of purification and/or drying, advantageously by freeze-drying or spray-drying, of the peptide of SEQ ID NO: 1 are carried out in an aqueous solution comprising an organic solvent" is that the solutions in which the peptide of SEQ ID NO: 1, in particular in the form of its salt, is dissolved after solid phase synthesis and optional precipitation, contain at all times an organic solvent.

This means in particular that any step aiming at reducing the volume of the aqueous solution containing the peptide of SEQ ID NO: 1 should be stopped before all the organic solvent is eliminated from said aqueous solution.

Advantageously, the organic solvent comprised in the aqueous solution is acetonitrile.

In the process according to the invention, acetonitrile is the solvent of choice because it can be used during the purification step, in particular as a mobile phase during chromatographic purification of the peptide and it enables reducing the dimerization of the peptide of SEQ ID NO: 1.

The volume of organic solvent, in particular acetonitrile, in the aqueous solution is advantageously maintained and/or adjusted in such a way that it represents in proportion from 1 to 90%, notably from 1 to 10%, of the total volume of the aqueous solution during the purification and optional concentration. Preferably, the aqueous solution contains about 5% of organic solvent, in particular acetonitrile.

The volume of organic solvent, in particular acetonitrile, in the aqueous solution to be dried, advantageously by freeze-drying or spray-drying, is maintained and/or adjusted in such a way that it represents in proportion from 1 to 30%, notably from 1 to 10%, preferably of about 5%, of the total volume of the aqueous solution.

In the context of the present invention, "the aqueous solution to be dried", is the aqueous solution containing the peptide of SEQ ID NO: 1 after the purification steps. It defines the aqueous solution that is subjected to the drying step.

In a second embodiment, the present invention concerns a process as described above, comprising the following steps:
 a) grafting of a Fmoc-Gly residue to a resin,
 b) elongation of the peptide chain with Fmoc-protected amino-acids in which the side chain is protected,
 c) simultaneous deprotection of the side chains of the amino-acids and cleavage of the polypeptide from the resin, to obtain the polypeptide of SEQ ID NO: 1,
 d) optional precipitation of the peptide of SEQ ID NO: 1,
 e) purification and optional concentration of the peptide of SEQ ID NO: 1,
 f) drying, advantageously by freeze-drying or spray-drying, of the peptide of SEQ ID NO: 1 obtained in step e).

The first glycine residue may be grafted onto virtually any resin known to those skilled in the art in step a), for example a Wang resin or a modified Wang resin.

Advantageously, the resin is a divinylbenzene-crosslinked polystyrene resin comprising 4-methylbenzhydrylamine groups, as it enables the cleavage of the peptide under less severe conditions. Said crosslinked resins are known to those skilled in the art and have been described, for example, in such publications as Peptides: Chemistry and Biology, 2nd Edition (DOI: 10.1002/9783527626038). These resins are commercially available, for example from suppliers such as Sigma-Aldrich or Polypeptide Laboratories. Resins directly functionalized by the linker and optionally the first amino acid can also be obtained commercially.

Advantageously, the first glycin residue is grafted onto the resin via a spacer. By "spacer", it is meant in the sense of the present invention a chain located between the resin and the carbonyl group of the first amino-acid.

More advantageously, the Fmoc-Gly residue is grafted onto the resin via the carbonyl function by a methylphenoxypropionic acid (MPPA) spacer under conventional reaction conditions.

Alternatively, a hydroxymethylphenoxyacetic acid (HMPA) spacer may be used instead of MPPA.

Once the first residue is fixed to the resin, the peptide is synthesized by using an iterative method consisting of sequences of (deprotection of the Fmoc group)/(coupling with an amino-acid protected by a Fmoc group on the amine and a protecting group on the side chain)/purification, until the protected (on the side chains) dodecapeptide of sequence SEQ ID NO: 1 is obtained.

These iterative methods of peptide synthesis can be carried out under conventional conditions well known to those skilled in the art, for example under the conditions described in the examples of the present application. In particular, the DIC/HOBt system may be used to carry out the peptide coupling. The deprotection of the Fmoc group is advantageously carried out with diisopropylethylamine (DIPEA).

In an embodiment, the amino-acids have their side chains protected with specific groups. As explained previously, the choice of appropriate protective groups is not trivial in peptide synthesis.

Advantageously, the present invention concerns a process as described above, in which:
 the protecting group of the side chain of Arg is a 2,2,4,6,7-pentamethyldihydrobenzofuran-5-sulfonyl,
 the protecting group of the side chain of Cys is a trityl,
 the protecting group of the side chain of Ser is a t-butyl,
 the protecting group of the side chain of Trp is a t-butoxycarbonyl.

Using these particular protecting groups, it has been found that the deprotection and cleavage from the resin step can be efficiently carried out.

The protected dodecapeptide bonded to the resin is then subjected to reaction conditions which make it possible to carry out simultaneously the cleavage of the C-terminal amino acid of the resin and the deprotection of the side chains of the amino acids constituting it. Unexpectedly, it has been demonstrated that in spite of the presence of potentially problematic amino acids, the deprotection of the side chains of the amino acids and the simultaneous cleavage of the polypeptide from the resin can be implemented with a mixture containing, as reagents, trifluoroacetic acid, water and 1,4-dithiothreitol. Advantageously, said mixture consists in, by weight of the total weight of the mixture, 85 to 95% of trifluoroacetic acid, 3 to 10% of 1,4-dithiothreitol and water up to 100%.

At the end of the deprotection and cleavage from the resin, the reaction medium contains the peptide of SEQ ID NO: 1, the cleavage and deprotection reagents and the by-products resulting from said deprotection step.

The product may be either directly purified by a chromatographic method or subjected to one or more purification steps and then optionally purified by a chromatographic method.

In an advantageous embodiment, the mixture containing the peptide of SEQ ID NO: 1 is subjected to a precipitation step. In the context of preparing the peptide of SEQ ID NO: 1, it has been demonstrated that the conventionally used solvents such as ethers lead to the formation of a gel preventing the isolation of the crude peptide of SEQ ID NO: 1. The inventors have discovered that the use of a mixture of an ether, in particular methyl-tert-butyl ether (MTBE) and an alkane, in particular heptane, makes it possible to partially purify the peptide of SEQ ID NO: 1. Advantageously, a 1:1 mixture of an ether and an alkane is used. More advantageously, a mixture of heptane and MTBE in a 1:1 ratio is used.

The peptide of SEQ ID NO: 1 as obtained at the end of step c) or step d), preferably after the precipitation step d) as defined above, is then subjected to purification. Said purification may be performed by any means known to those skilled in the art, provided that it affords a product having the sufficient purity for further administration to a patient.

Advantageously, the purification step is achieved by at least one preparative reverse phase chromatography. The conditions (i.e. stationary phase, mobile phase, flow) can be determined by the one skilled in the art. Preparative chromatography is an effective method for providing a product having a purity sufficient for administration to the patients, advantageously greater than 90%, in particular greater than 95% as determined by analytical means such as HPLC, NMR and/or GC.

The preparative reverse phase chromatography is typically carried out using trifluoroacetic acid in the mobile phase. The product obtained is therefore the trifluoroacetate salt of the peptide of SEQ ID NO: 1.

The process may therefore comprise a further step of ion exchange to replace the trifluoroacetate ion by another ion, in particular to obtain a pharmaceutically acceptable salt.

By "pharmaceutically acceptable salt", it is meant in the sense of the present invention, a salt that is generally safe, non-toxic and neither biologically nor otherwise undesirable, is acceptable for administration to human and possesses the desired pharmacological activity of the parent compound. Said salts can be used for modifying the solubility or hydrolysis characteristics or can be used in sustained release or pro-drug formulations. These salts may be prepared by standard procedures, e.g. by reacting a free acid with a suitable organic or inorganic base Such salts include acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, sulfate, sulfonate, tannate, hydrochloride, tartrate, triflate, hydroxynaphthoate, teoclate, iodide, tosylate, isothionate, triethiodide, lactate, pamoate, valerate.

Advantageously, the ion exchange may be performed by reverse phase chromatography using the corresponding acid in the mobile phase or on an ion exchange resin. More advantageously, said ion exchange may be done on a reverse phase chromatographic stationary phase. In particular, said ion exchange may be done continuously to the purification by preparative reverse phase chromatography.

Within the context of the present invention, "continuously" means that the aqueous solution obtained in step e) and containing the peptide is subjected to the ion exchange procedure without concentration of the aqueous solution, for example by evaporation of the solvent or any other mean known to those skilled in the art.

Preferably, said ion exchange step is performed on the same stationary phase as the one used for the purification of the product (after regeneration of said stationary phase).

The peptide of SEQ ID NO: 1 is eventually dried after purification. The peptide may be dried by any means known to those skilled in the art, provided that it does not affect the purity of the product.

Advantageously, the peptide of SEQ ID NO: 1 is dried by freeze-drying or spray-drying. These drying methods are gentle and avoid degradation of the product. As found by the Inventors, the presence of an organic solvent, in particular acetonitrile, at the beginning of the drying step is essential to prevent dimerization of the peptide of SEQ ID NO: 1.

The volume of organic solvent, in particular acetonitrile, in the aqueous solution at the beginning of the drying step, advantageously the freeze-drying step or spray-drying step, is maintained and/or adjusted in such a way that it represents in proportion from 1 to 30%, notably from 1 to 10%, preferably of about 5%, of the total volume of the aqueous solution.

The present invention therefore concerns a process as defined above in which the peptide of SEQ ID NO: 1 in an aqueous solution comprising from 1 to 30%, notably from 1 to 10%, preferably about 5%, of the total volume of the aqueous solution, of an organic solvent, in particular acetonitrile, is dried, preferably by freeze-drying or spray-drying.

The present invention preferably concerns a process as described above for preparing a peptide of SEQ ID NO: 1, comprising the following steps:

a) grafting of a Fmoc-Gly-MMPA-OH residue to a divinylbenzene-crosslinked polystyrene resin comprising 4-Methylbenzhydrylamine groups, b) elongation of the peptide chain with Fmoc protected cys, ser, arg, ser, cys, ser, ser, trp, gly, ser, and trp, in which the protecting group of the side chain of Arg is a 2,2,4,6,7-pentamethyldihydrobenzofuran-5-sulfonyl, the protecting group of the side chain of Cys is a trityl, the protecting group of the side chain of Ser is a t-butyl, the protecting group of the side chain of Trp is a t-butoxycarbonyl, to obtain a peptide of SEQ ID NO: 1 in which the side chains are protected.

c) simultaneous deprotection of the side chains of the amino-acids and cleavage of the polypeptide from the resin, with a mixture of trifluoroacetic acid, water and 1,4-dithiothreitol, to obtain the polypeptide of SEQ ID NO: 1 d) precipitation of the peptide of SEQ ID NO: 1 with a mixture of heptane and MTBE, e) purification of the peptide of SEQ ID NO: 1 by preparative reverse phase chromatography, characterised in that the peptide of SEQ ID NO: 1 is constantly maintained in an aqueous solution comprising an organic solvent, preferably acetonitrile, f) concentration of the solution containing the peptide of SEQ ID NO: 1 obtained in step e), to obtain a concentrated aqueous solution containing the peptide of SEQ ID NO: 1 and an organic solvent, preferably acetonitrile, g) exchange of the trifluoroacetate ion with a pharmaceutically acceptable ion, notably an acetate, on a reverse phase chromatographic stationary phase or on an ion exchange resin, h) concentration of the aqueous solution containing the peptide of SEQ ID NO: 1 obtained in step g), to obtain a concentrated aqueous solution containing the peptide of SEQ ID NO: 1 and an organic solvent, preferably acetonitrile, i) drying, advantageously by spray-drying or freeze-drying, of the aqueous solution obtained in step h), to obtain the peptide of SEQ ID NO: 1.

In a second embodiment, the present invention concerns the use of an organic solvent, notably acetonitrile, in an aqueous solvent for preventing the dimerization of a peptide of SEQ ID NO: 1, in particular during purification, optional concentration and drying, advantageously by spray drying of freeze drying, of a peptide of SEQ ID NO: 1.

EXAMPLES

Example 1

Figure 1:
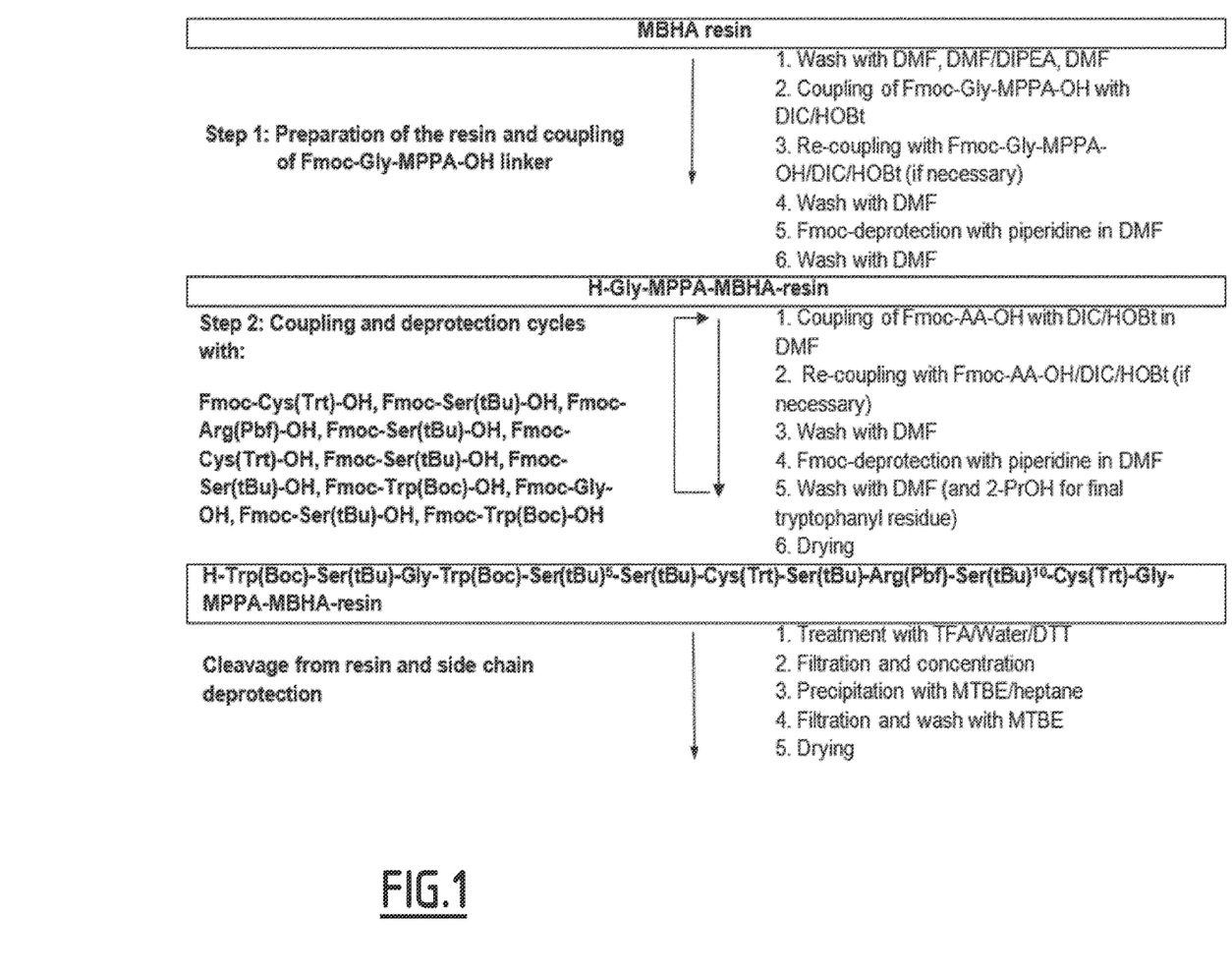
FIG. 1 represents the general scheme for the preparation of the dodecapeptide of SEQ ID NO.
Figure 2A:
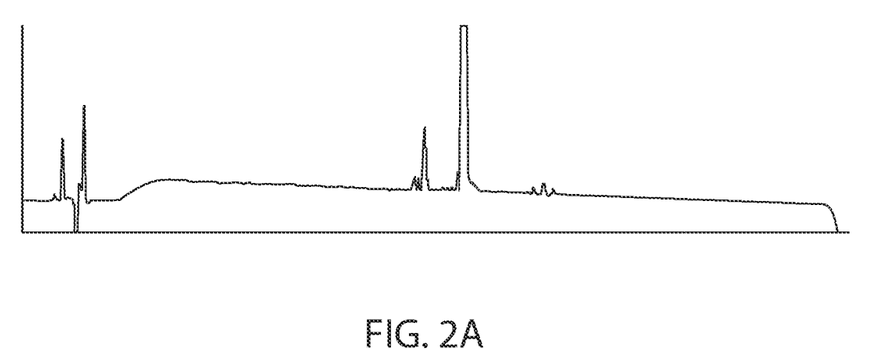
FIG. 2A shows the chromatogram obtained when the process is carried out using acetonitrile in the ad hoc steps, i.e. purification and drying.
Figure 2B:
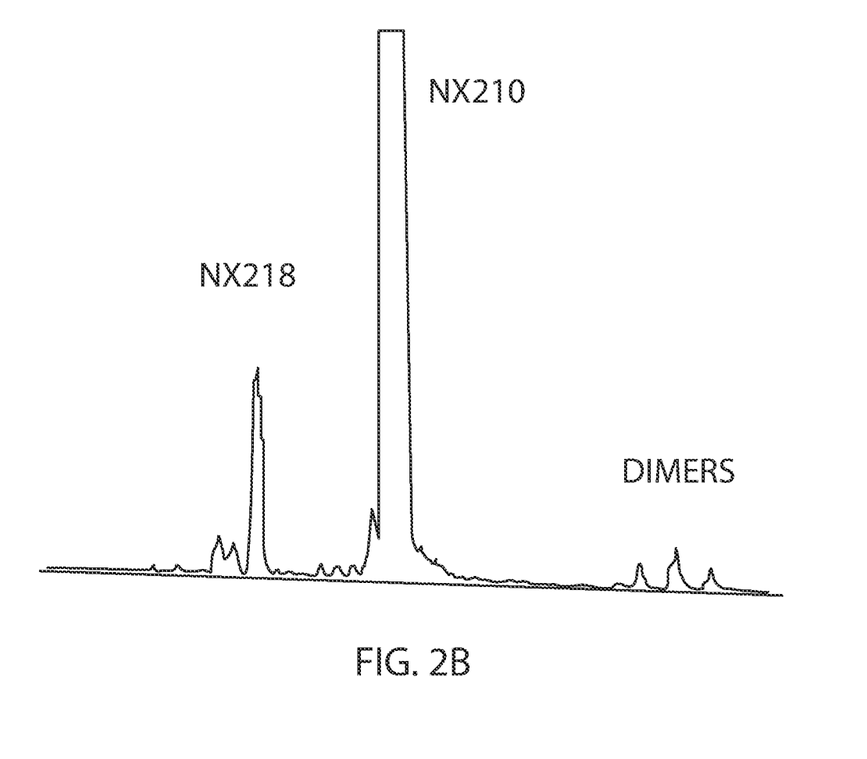
FIG. 2B shows an enlargement of the chromatogram showing the peaks for NX218, NX210, and dimers.
Figure 3A:
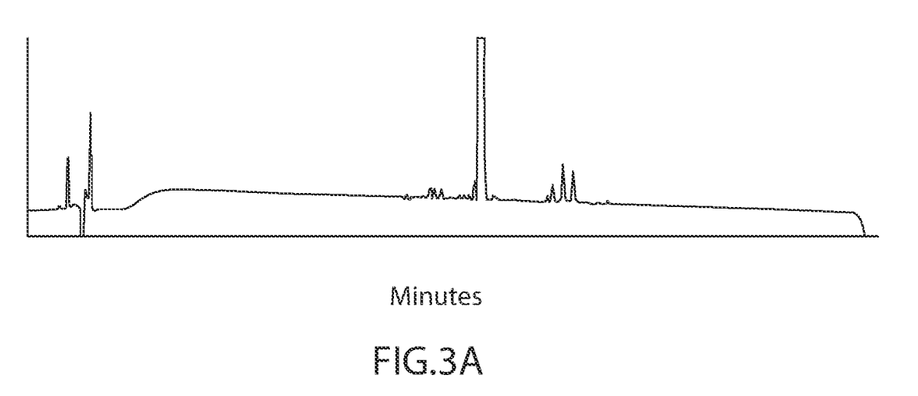
FIG. 3A shows the chromatogram obtained when the process is carried out without using acetonitrile during the purification, drying and chromatographic steps.
Figure 3B:
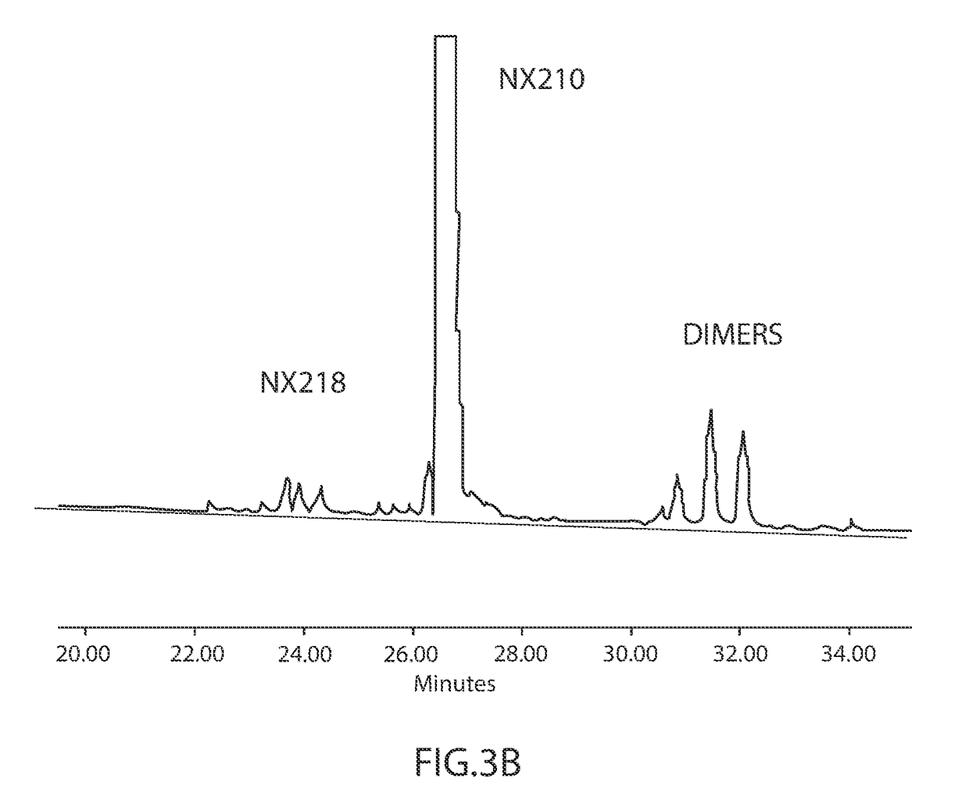
FIG. 3B shows an enlargement of chromatogram showing the peaks for NX218, NX210, and dimers.

Preparation of the Peptide of SEQ ID NO: 1

The following reagents were used:

TABLE 1 amino acids used (all amino acids have an L configuration)

| Abbreviation | Role |
| --- | --- |
| Fmoc-Arg(Pbf)-OH | Protected amino-acid |
| Fmoc-Cys(Trt)-OH | Protected amino-acid |
| Fmoc-Gly-OH | Amino-acid |
| Fmoc-Gly-MPPA-OH | Amino-acid-linker-OH |
| Fmoc-Ser(tBu)-OH | Protected amino-acid |
| Fmoc-Trp(Boc)-OH | Protected amino-acid |

TABLE 2 reagents and solvents used for peptide synthesis

| Name | Abbreviation | Role |
| --- | --- | --- |
| N,N-Dimethylformamide | DMF | Solvent |
| N,N-Diisopropylethylamine | DIPEA | Reagent |
| Piperidine | — | Reagent |
| N,N'-Diisopropylcarbodiimide | DIC | Reagent |
| N-Hydroxybenzotriazole hydrate | HOBt | Reagent |
| 2-Propanol | 2-PrOH | Solvent |
| Nitrogen (gaz) | $N_2$ | Inert atmosphere |

TABLE 3 reagents and solvents used for cleavage from the resin and deptorection

| Name | Abbreviation | Role |
| --- | --- | --- |
| Trifluoroacetic acid | TFA | Reagent |
| Dithiothreitol | DTT | Reagent |
| Heptane | — | Solvent |
| Methyl-tert-butyl ether | MTBE | Solvent |
| Nitrogen (gas) | $N_2$ | Inert atmosphere |
| Water | $H_2O$ | Reagent and solvent |

TABLE 4 reagents and solvents used for purification, ion conversion by reverse phase chromatography and lyophilisation

| Name | Abbreviation | Role |
| --- | --- | --- |
| Trifluoroacetic acid | TFA | Reagent |
| Acetic acid | AcOH | Reagent |

TABLE 4-continued reagents and solvents used for purification, ion conversion by reverse phase chromatography and lyophilisation

| Name | Abbreviation | Role |
| --- | --- | --- |
| Acetonitrile | $CH_3CN$ | Solvent |
| Water | $H_2O$ | Solvent |
| Ammonium acetate | $NH_4OAc$ | Reagent |
| 2-Propanol | 2-PrOH | Solvent for chromatography column packing |

TABLE 5

Resin used

| Name | Abbreviation | Role |
| --- | --- | --- |
| p-Methylbenzhydrylamine polystyrene-1% divinylbenzene Resin | MBHA Resin | Solid phase peptide synthesis resin (SPPS) |
| Silica $C_{18}$ resin | — | Stationary phase for reverse phase chromatography |

The manufacturing process of NX210 is based on Solid-Phase Peptide Synthesis (SPPS) applying N-α-Fmoc (side chain) protected amino acids as building blocks in the assembly of the peptide.

The protocol employed consists of a coupling of the C-terminal Glycine N-α-Fmoc-protected amino acid bound to an MPPA linker on the MBHA resin, followed by Fmoc coupling/deprotection sequences.

After assembly of the peptide on the resin, a step of simultaneous cleavage of the peptide from the resin and deprotection of the side chains of the amino-acid is carried out.

The crude peptide of SEQ ID NO: 1 is precipitated, filtered and dried. Prior to purification by preparative reverse phase chromatography, the peptide of SEQ ID NO: 1 is dissolved in a aqueous solution containing acetonitrile. The purified peptide in solution is then concentrated before undergoing an ion exchange step to give the peptide of SEQ ID NO: 1 in the form of its acetate salt.

Step 1: Assembling the Peptide:

The first glycine residue is coupled to the resin in the form of Fmoc-Gly-MPPA-OH with the DIC/HOBt system in DMF (ratio MBHA/FmocGlyMPPA/DIC/HOBt: 1, 1.35, 1.35, 1.35).

Prior to each coupling step, the Fmoc-protecting group is removed with 25% piperidine in DMF and the resin is washed with DMF so as to remove the excess piperidine. Coupling of the Fmoc-protected amino acid is accomplished using the DIC/HOBt system in DMF.

After completion of the coupling with one amino acid, the next coupling is carried out under similar conditions.

After coupling of the tryptophan terminal amino acid and deprotection of the terminal Fmoc group, the resin is washed with DMF and 2-propanol and dried to constant mass.

Step 2: Concomitant Cleavage of the Peptide from the Resin and Deprotection of the Side Chains:

Various conditions for deprotection and cleavage have been employed. The best results were obtained with the trifluoroacetic acid/water/1,4-dithiothreitol cocktail (86/5/9 v/v/m). The resin is then removed by filtration, the peptide remaining in solution with a complex mixture of reagents and by-products.

Step 3: Precipitation of the Peptide and Filtration Prior to Purification by HPLC:

The volume of the filtrate containing the peptide of SEQ ID NO: 1 is reduced and the peptide is precipitated using a mixture of MTBE and heptane. The use of other solvents which are conventionally used (e.g. diethyl ether or MTBE alone) leads to the formation of a gel which cannot be filtered.

After filtration, the solid is dried under reduced pressure until constant mass.

Step 4: Dissolution of the Precipitate Before Purification by HPLC:

Before purification, the impure NX210 obtained by precipitation is dissolved in an acetonitrile/water/acetic acid mixture.

The addition of acetonitrile to the aqueous solution is critical to obtaining the peptide with a sufficiently high purity level. Indeed, it has been observed that with a water/acetic acid mixture, the formation of the dimer is increased. These dimers lead to the formation of more complex oligomers which are no longer suitable for therapeutic development because of their propensity to form aggregates incompatible in particular with intrathecal direct administration.

Such an effect of acetonitrile at the time of dissolution is particularly unusual and to date unexplainable. Another consequence is the discovery that the analyses of the product require the product to be dissolved in a mixture containing acetonitrile in order to be reliable and to reflect the actual impurity content of the product, whatever the operator of the measurement.

Step 5: First Purification by HPLC:

The purification and conversion to the acetate salt are carried out in two stages without intermediate purification by reverse phase HPLC. The NX210 as obtained in step 4 is adsorbed onto the column and eluted from the column with a gradient of acetonitrile in dilute aqueous trifluoroacetic acid (at room temperature).

Chromatography is carried out under the following conditions:

Column: LC110 multi-purpose (stationary phase Luna® C18 grafted silica, 15 μm, 100 Å, about 1250 g for 12 g of crude NX210 injected, ie a charge of about 1%).

Flow: 450 mL/min

Elution gradient: 7-32% mobile phase (0.1% acetic acid in acetonitrile/water (80/20, v/v) over 30 minutes.

The choice of the stationary phase, the injection charge, the flow rate and the gradient can of course be adapted to improve the separation of the impurities.

Step 6: Second Purification and Conversion to Acetate Salt:

The second purification and conversion to acetate is carried out by preparative reverse phase CHLP on a multi-purpose LC110 column. The stationary phase is Luna® C18 grafted silica (15 μm, 100 Å, about 1250 g for 19 g of injected crude peptide). The filling and washing of the column are carried out.

Example 2

Comparative Tests

The importance of the addition of acetonitrile in the purification steps was evaluated. The same procedure as that of Example 1 was carried out by evaporating the acetonitrile between the steps and omitting the acetonitrile prior to freeze-drying.

The results are given in the table below:

| Impurity | Phase | Peak intensity | Increase (%) |
| --- | --- | --- | --- |
| Dimer 1 | Acetonitrile | 0.05 | |
| | Water | 0.15 | 300 |
| Dimer 2 | Acetonitrile | 0.31 | |
| | Water | 1.21 | 390 |
| Dimer 3 | Acetonitrile | 0.14 | |
| | Water | 0.98 | 700 |
| Trimers | Acetonitrile | Below detection limit | |
| | Water | 0.07 | n/a |

As shown by the results of the analysis, in the absence of acetonitrile, the product obtained at the end of the preparation process contains a significantly higher proportion of dimers. Without acetonitrile, trimeric species are also observed during the analysis.

The invention claimed is:

1. A process for preparing a peptide of SEQ ID NO: 1, comprising:
   a) grafting of a Fmoc-Gly-MMPA-OH residue to a divinylbenzene-crosslinked polystyrene resin comprising 4-Methylbenzhydrylamine groups,
   b) elongation of the peptide chain with Fmoc protected Cys, Ser, Arg, Ser, Cys, Ser, Ser, Trp, Gly, Ser, and Trp, in which the amino acids Cys, Ser, Arg and Trp have a side chain which is protected, wherein the protecting group of the side chain of Arg is a 2,2,4,6,7-pentamethyldihydrobenzofuran-5-sulfonyl, the protecting group of the side chain of Cys is a trityl, the protecting group of the side chain of Ser is a t-butyl, and the protecting group of the side chain of Trp is a t-butoxycarbonyl, to obtain a peptide of SEQ ID NO: 1 in which the side chains of amino acids Cys, Ser, Arg and Trp are protected,
   c) simultaneous deprotection of the side chains of the protected amino-acids and cleavage of the peptide from the resin, with a mixture of trifluoroacetic acid, water and 1,4-dithiothreitol, to obtain the peptide of SEQ ID NO: 1,
   d) precipitation of the peptide of SEQ ID NO: 1 with a mixture of heptane and MTBE,
   e) putting the peptide of SEQ ID NO: 1 in an aqueous solution containing acetonitrile, and purification of the peptide of SEQ ID NO: 1 contained in this solution by preparative reverse phase chromatography using an aqueous solution of trifluoroacetic acid as eluent, recovering the peptide of SEQ ID NO: 1 as a trifluoroacetate salt,
   f) dilution of the product of e) with water,
   g) exchange of a trifluoroacetate ion with a pharmaceutically acceptable ion, on a reverse phase chromatographic stationary phase or on an ion exchange resin, recovering an aqueous solution containing the peptide of SEQ ID NO: 1 and acetonitrile,
   h) the product of g) containing the peptide of SEQ ID NO: 1 and acetonitrile is diluted with water, then concentrated, and then combined with an aqueous solution containing 1 to 10% of acetonitrile in volume to obtain an aqueous solution containing the peptide of SEQ ID NO: 1 and acetonitrile, and
   i) drying of the aqueous solution obtained in h), to obtain the peptide of SEQ ID NO: 1.

2. The process of claim 1, wherein the product of g) comprises the peptide of SEQ ID NO: 1 as an acetate salt, diluted in water, then concentrated, and then combined with an aqueous solution of 1 to 10% of acetonitrile in volume, and then said aqueous solution is subject to drying.

3. The process of claim 1, wherein the drying according to i) is freeze-drying or spray-drying.

4. The process of claim 2, wherein the drying is freeze-drying or spray-drying.

5. A process for preparing a peptide of SEQ ID NO: 1, comprising:
   a) grafting of a Fmoc-Gly residue to a resin,
   b) elongating the peptide chain with Fmoc-protected Cys, Ser, Arg, Ser, Cys, Ser, Ser, Trp, Gly, Ser, and Trp, in which amino acids Cys, Ser, Arg and Trp have a side chain which is protected,
   c) simultaneously deprotecting the side chains of the protected amino-acids and cleavage of the peptide from the resin, to obtain the peptide of SEQ ID NO: 1,
   d) purifying and concentrating the peptide of SEQ ID NO: 1, comprising
      d1) putting the peptide of SEQ ID NO: 1 in an aqueous solution containing acetonitrile, and purification of the peptide of SEQ ID NO: 1 contained in this solution by preparative reverse phase chromatography using an aqueous solution of trifluoroacetic acid as eluent, recovering the peptide of SEQ ID NO: 1 as a trifluoroacetate salt,
      d2) dilution of the product of d1) with water,
      d3) exchange of a trifluoroacetate ion with a pharmaceutically acceptable ion, on a reverse phase chromatographic stationary phase or on an ion exchange resin, recovering an aqueous solution containing the peptide of SEQ ID NO: 1 and acetonitrile, and
      d4) the product of d3) containing the peptide of SEQ ID NO: 1 and acetonitrile is diluted with water, then concentrated, and then combined with an aqueous solution containing 1 to 10% of acetonitrile in volume to obtain an aqueous solution containing the peptide of SEQ ID NO: 1 and acetonitrile, and
   e) drying of the aqueous solution obtained in d4), to obtain the peptide of SEQ ID NO: 1.

6. The process of claim 5, wherein the product of d3) comprises the peptide of SEQ ID NO: 1 as an acetate salt, diluted in water, then concentrated, and then combined with an aqueous solution of 1 to 10% of acetonitrile in volume, and then said aqueous solution is subject to drying.

7. The process of claim 5, wherein the drying according to e) is freeze-drying or spray-drying.

8. The process of claim 6, wherein the drying is freeze-drying or spray-drying.

* * * * *

SEQUENCE LISTING

<160> NUMBER OF SEQ ID NOS: 1

<210> SEQ ID NO 1
<211> LENGTH: 12
<212> TYPE: PRT
<213> ORGANISM: Artificial Sequence
<220> FEATURE:
<223> OTHER INFORMATION: NX210

<400> SEQUENCE: 1

Trp Ser Gly Trp Ser Ser Cys Ser Arg Ser Cys Gly
1               5                   10